United States Patent [19]

Christensen et al.

[11] Patent Number: 4,582,643

[45] Date of Patent: * Apr. 15, 1986

[54] 6-(1-HYDROXYETHYL)-2-(2-AMINOETHYL-THIO)-1,1-DISUBSTITUTED-1-CARBADE-THIAPEN-2-EM-3-CARBOXYLIC ACIDS

[75] Inventors: Burton G. Christensen, Cliffside Park; David H. Shih, Manalapan, both of N.J.

[73] Assignee: Merck & Co., Inc., Rahway, N.J.

[ * ] Notice: The portion of the term of this patent subsequent to Aug. 19, 1997 has been disclaimed.

[21] Appl. No.: 397,734

[22] Filed: Jul. 13, 1982

Related U.S. Application Data

[60] Continuation-in-part of Ser. No. 208,353, Nov. 19, 1980, abandoned, which is a division of Ser. No. 99,288, Dec. 3, 1979, Pat. No. 4,262,010.

[51] Int. Cl.$^4$ .................. C07D 487/04; A61K 31/40
[52] U.S. Cl. ........................ 260/245.2 T; 514/210
[58] Field of Search ................ 260/245.2 T, 245.2 R; 424/270; 514/210

[56] References Cited

U.S. PATENT DOCUMENTS

| | | | |
|---|---|---|---|
| 4,194,047 | 3/1980 | Christensen et al. | 260/245.2 R |
| 4,206,219 | 6/1980 | Christensen et al. | 260/245.2 T |
| 4,218,462 | 8/1980 | Christensen et al. | 260/245.2 T |
| 4,312,871 | 6/1982 | Christensen et al. | 424/270 |

*Primary Examiner*—Nicholas S. Rizzo
*Attorney, Agent, or Firm*—Raymond M. Speer; Hesna J. Pfeiffer

[57] ABSTRACT

Disclosed are 1-substituted-6-(1-hydroxyethyl)-2-(2-aminoethylthio)-1-carbadethiapen-2-em-3-carboxylic acids (I) and their pharmaceutically acceptable salts and esters which are useful as antibiotics; such compounds are prepared by total synthesis.

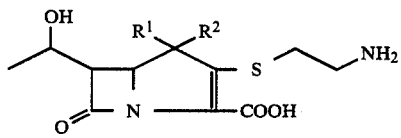

wherein $R^1$ and $R^2$ are, inter alia, substituted and unsubstituted alkyl, aryl, aralkyl, cycloalkyl, cycloalkylalkyl and the spiro substituent formed by the joinder of $R^1$ and $R^2$.

4 Claims, No Drawings

6-(1-HYDROXYETHYL)-2-(2-AMINOETHYLTHIO)-1,1-DISUBSTITUTED-1-CARBADETHIAPEN-2-EM-3-CARBOXYLIC ACIDS

BACKGROUND OF THE INVENTION

This is a continuation-in-part of U.S. Ser. No. 208,353 filed Nov. 19, 1980, now abandoned, which in turn is a division of U.S. Ser. No. 99,288 filed Dec. 3, 1979, now U.S. Pat. No. 4,262,010; said parental applications are fully incorporated herein by reference.

This invention relates to 6-(1-hydroxyethyl)-2-(2-aminoethylthio)-1,1-disubstituted-1-carbadethiapen-2-em-3-carboxylic acids (I) and their pharmaceutically acceptable salts and esters which are useful as antibiotics. This invention also relates to a process for preparing such compounds, (I):

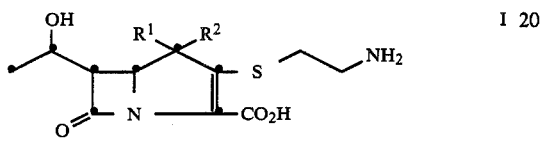

I wherein $R^1$ and $R^2$ are selected from the group consisting of substituted and unsubstituted: loweralkyl having from 1–6 carbon atoms; aralkyl such as phenylloweralkyl; aryl such as phenyl; cycloalkyl and cycloalkylalkyl having from 3–6 carbon atoms in the alkyl moiety and 3–6 carbon atoms in the ring; and spirocycloalkyl formed by the joinder of $R^1$ and $R^2$ wherein said ring or chain substituents on $R^1$ and $R^2$ are selected from the group consisting of hydroxyl, chloro, bromo, fluoro, iodo, amino, mono-, di-, and trialkylamino wherein the alkyl moiety has 1–6 carbon atoms; carboxyl; carbamoyl; ureido; amidino, guanidino, and the like.

With regard to said substituents on $R^1$ and $R^2$, the degree of substitution and patterns embrance all those feasible, starting with mono-substitution of either $R^1$ or $R^2$ and continuing through all permutations involving both $R^1$ and $R^2$ and all named substituents. Mono-substitution of either $R^1$, $R^2$ or both simultaneously is preferred.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as S. aureus, Strep. pyogenes and B. subtilis, and gram negative bacteria such as E. coli, Proteus morganii, Pseudomonas, Serratis and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The process of the present invention may conveniently be summarized by the following reaction diagram:

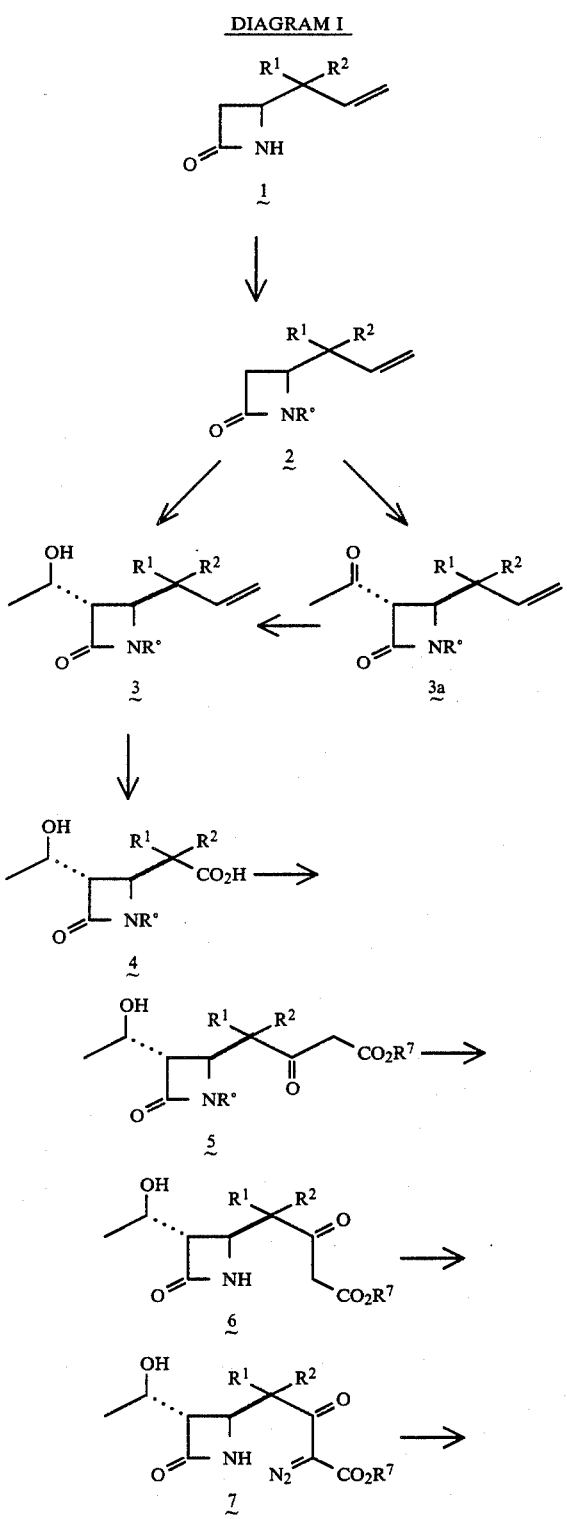

-continued
DIAGRAM I

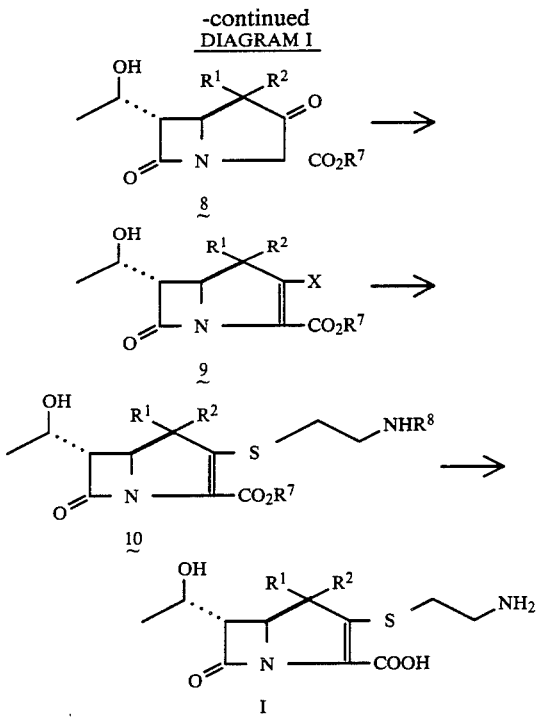

In words relative to Diagram I, starting material 1 is transformed (1→2) to establish the protecting group R° which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R° is established by treating 1 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from $-20°$ to $25°$ C. for from 0.5 to 24 hours in the presence of a base such as triethylamine, diisopropylethylamine, or imidazole.

The alkylation 2→3 is accomplished by treating 2 in a solvent such as tetrahydrofuran, dimethoxyethane, diethylether, hexamethylphosphoramide, at a temperature of from $-100°$ to $-20°$ C. with a strong base such as lithium diisopropylamide, lithium hexamethyldisilazide, lithium 2,2,6,6-tetramethylpiperidine, potassium hydride or the like followed by the addition of an equivalent to 10 fold excess of acetaldehyde. This reaction gives a mixture of isomers from which the desired trans-R form can be conveniently separated by chromatography or crystallization.

Intermediate 2 may proceed directly to 3, as indicated above, or it may take the circuitous path via 3a. The direct acetylation, to 3a is accomplished by treating 3 with two or more equivalents of a base such as lithium diisopropylamide, lithium hexamethyldisilazide, lithium 2,2,6,6-tetramethylpiperidine, in a solvent such as tetrahydrofuran, diethylether, or dimethoxyethane, for example, at a temperature of from $-100°$ to $-20°$ C. with an acylating agent such as N-acetyl imidazole or the like. Addition of the 3 plus base mixture to the acylating agent is preferred.

The reduction, 3a→3, is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethylether, tetrahydrofuran, toluene or the like at a temperature of from $-20°$ to $25°$ C. The reaction can conveniently be conducted in the presence of an added complexing salt such as potassium iodide, magnesium bromide or the like.

In a similar manner, unresolved 3 β') may be oxidized to 3a for reduction to 3 as indicated above:

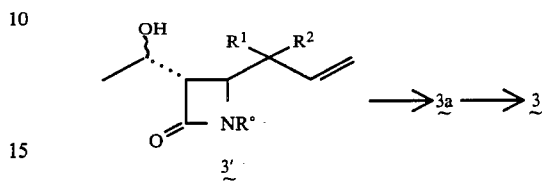

The oxidation (3'→3a) is accomplished with an oxidizing agent such as dipyridine chromium (VI) oxide, trifluoroacetic anhydride-dimethylsulfoxidetriethylamine, pyridinium dichromate, acetic anhydridedimethylsulfoxide in a solvent such as methylene chloride, acetonitrile, or the like at a temperature of from $-78°$ to $25°$ C. for from 5 minutes to 5 hours.

The oxidation 3→4 is accomplished by treating 3 in a solvent such as methylenechloride, methanol, chloroform, or the like, with an oxidizing agent such as ozone, or the like, at a temperature of from $-100°$ to $0°$ C. for from 0.1 to 4 hours, followed by treating the crude product with an oxidizing agent such as m-chloroperchenzoic acid, hydrogen peroxide, peracetic acid, or the like, at a temperature of from $0°$ C. to $100°$ C. for from 1 to 100 hours.

Intermediate species 4 is racemic. Resolution to obtain the (1') R, 3S, 4R-isomer is conveniently conducted at this point. Such resolution may be achieved by any of a variety of known procedures, such as: physical separation via crystallization, chromatography of the diasteomeric salts formed on reaction of 4 with an appropriate optically active amine such as bracine, ephedsine, strychnine, morphine, or the like.

The addition 4→5 is accomplished by treating 4 with 1,1'-carbonyldiimidazole, or the like, in a solvent such as tetrahydrofuran, dimethoxyethane, or the like, at a temperature of from $0°$ to $50°$ C., followed by the addition of 1.1 to 3.0 equivalent of $(R^7O_2CCH_2CO_2)_2Mg$, at a temperature of from $0°$ to $50°$ C. for from 1 to 48 hours. $R^7$ is a readily removable carboxyl protecting groups such as p-nitrobenzyl, benzyl, or the like.

Removal of protecting group R° (6→6) is accomplished by acidic aqueous hydrolysis of 5 in a solvent such as methanol, ethanol, tetrahydrofuran, dioxane, or the like, in the presence of an acid such as hydrochloric, sulfuric, acetic or the like at a temperature of from $0°$ to $100°$ C. for from 2 to 18 hours.

The diazo species 7 is prepared from 6 by treating 6 in a solvent such as $CH_3CN$, $CH_2Cl_2$, THF, or the like, with an azide such as p-carboxybenzenesulfonylazide, toluenesulfonylazide, methanesulfonylazide, or the like, in the presence of a base such as triethylamine, pyridine, $(C_2H_5)_2NH$, or the like, for from 1 to 50 hours at $0°$–$25°$ C.

Cyclization (7→8) is accomplished by treating 7 in a solvent such as benzene, toluene, THF, or the like, at a temperature of from $50°$–$110°$ C. for from 1–5 hours in the presence of a catalyst such as bis (acetylacetonato)-Cu(II) [Cu(acac)$_2$], $CuSO_4$, Cu powder, $Rh(OAc)_2$ or Pd(OAC)$_2$. Alternatively, the cyclization may be accomplished by irradiating 7 through a pyrex filter (a wave length greater than 300 nm) in a solvent such as benzene, CCl$_4$, diethylether, or the like, at a temperature of from 0°–25° C. for from 0.5 to 2 hours. ["OAc"-=acetate.]

Establishment of leaving group X (8→9) is accomplished by acylating the keto ester 8 with an acylating agent RX such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like wherein X is the corresponding leaving group such as toluene sulfonyloxy, p-nitrophenylsulfonyloxy, methanesulfonyloxy, p-bromophenylsulfonyloxy and other leaving groups which are established by conventional procedures and are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylamino-pyridine or the like at a temperature of from −20° to 40° C. for from 0.5 to 5 hours. The leaving group X of intermediate 9 can also be halogen. The halogen leaving group is established by treating 8 with a halogenating agent such as $\phi_3$PCl$_2$, $\phi_3$PBr$_2$, ($\phi$O)$_3$PBr$_2$, oxalyl chloride or the like in a solvent such as CH$_2$Cl$_2$, CH$_3$CN, THF, or the like in the presence of a base such as diisopropylethylamine, triethylamine, or 4-dimethylaminopyridine or the like. [$\phi$=phenyl.]

The reaction 9→10 is accomplished by treating 9 in a solvent such as dioxane, dimethylformamide, dimethylsulfoxide, acetonitrile, hexamethylphosphoramide, or the like in the presence of an approximately equivalent to excess of the mercaptan reagent HSCH$_2$CH$_2$NHR$^8$ wherein R$^8$ is hydrogen or a readily removable N-protecting group such as p-nitrobenzyloxycarbonyl, o-nitrobenzyloxycarbonyl, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, HSCH$_2$CH$_2$NHR$^8$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 10→I is accomplished by conventional procedures such as hydrolysis or hydrogenation. Typically 10 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, or the like at a temperature of from 0° to 50° C. for from 0.5 to 4 hours to provide I.

Preparation of Starting material 1

Starting material 1 is conveniently prepared by the following scheme:

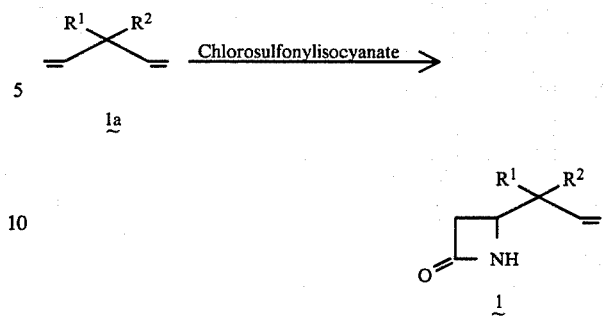

In words relative to the above diagram, the substituted azetidinone 1 is prepared by reacting a 3-substituted 1,4-pentadiene with chlorosulfonylisocyanate at 25° to 60° C. in a pressure bottle for 3–12 days, then the resulting mixture is hydrolyzed with aqueous sodium sulfite solution between pH 6.5–7.5 at 0° C. to 25° C. for from 5 min. to 60 min.

With respect to starting reagent 1a, its preparation is generally described in J. Amer. Chem. Soc. 74, 661 (1952) by E. B. Reid and T. E. Gompf; J. Org. Chem., 23, 1063 (1958) by R. Ciola and K. L. Burwell, Jr.; and Belgium Pat. No. 632,193 (1963) of R. Polster and E. Scharf. The following scheme summarizes the preparation of 1a.

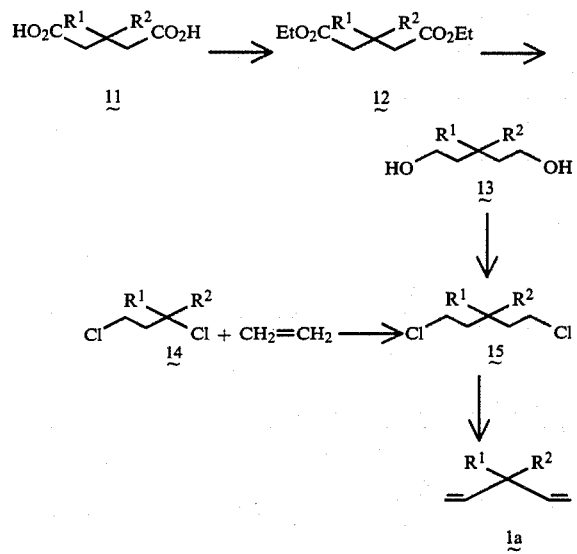

In words relative to the above scheme, the diester 12 is prepared by treating the diacid 11 with thionyl chloride at reflux for two hours followed by reacting with ethanol at 80° C. for 4 hours. Reduction of the diester 12 with lithium aluminum hydride in ether at reflux for 4 hours followed by hydrolysis with 10% NaOH gives diol 13 which on further reaction with thionyl chloride, gives the dichloride 15. The dichloride 15 can be alternatively prepared by treating 14 with ethylene in the presence of aluminum chloride. Treatment of the dichloride 15 with base such as 2-methylquinoline, DBU or sodium hydroxide in polyethylene glycol gives the expected 3-substituted 1,4-pentadiene 1a.

Especially preferred embodiments of the present invention are those wherein R$^1$ and R$^2$ are selected from the group consisting of methyl, ethyl, propyl, isopropyl, cyclopropyl, phenyl, benzyl, and 2-bromoethyl, spirocyclopropyl.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae, Serratia, Salmonella typhosa*, Pseudomonas and *Bacterium proteus*. The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination with other active ingredients in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oil suspension, solution, emulsions, or groups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water before use.

The compositions may also be prepared in suitable forms for absorption through the mucous membranes of the nose and throat or bronchial tissues and may conveniently take the form of powder, liquid sprays, inhalants, lozenges, or throat paints. For medication of the eyes or ears, the preparations may be presented as individual capsules, in liquid or semi-solid form, or may be used as drops etc. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredients per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in U.S. patent application Ser. No. 861,314 (filed 12-16-77) which application is directed, inter alia, to pharmaceutically acceptable salts and esters of the carboxyl group of thienamycin. It is precisely these salts and esters which are preferred in the present invention and they are prepared in a manner analogous to that disclosed in U.S. patent application Ser. No. 861,314, which is incorporated herein by reference. Thus, especially preferred salts include sodium, potassium, ammonium, and the like; and especially preferred esters include pivaloxymethyl, p-t-butylbenzyl, 5-indanyl, 3-phthalidyl, 3-methyl-2-butenyl, and the like. One should note that when, in the total synthesis outlined above, $R^7$ is a pharmaceutically acceptable ester moiety, there is no need for the final deblocking step if it is desired to have the final product I in the form of a pharmaceutically acceptable ester.

Especially preferred embodiments of the present invention are those, as defined above, except that the amino group on the aminoethylthio side chain of Structure I is derivatized according to the teachings of Belgium Pat. No. 848,545 (issued 5-20-77); the resulting amino group being represented thusly (partial structure):

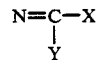

wherein X and Y are defined by the publication; species wherein X is H or lower alkyl and Y is NH₂ are especially preferred.

In the foregoing word description of the above schematic reaction diagram for the total synthesis of 6-(1-hydroxyethyl)-2-(2-aminoethylthio)-1-substituted-1-carbadethiapen-2-em-3-carboxylic acids is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

Preparation of 1-(t-Butyldimethylsilyl)-4-(1,1-dimethylprop-2-enyl)-azetidin-2-one

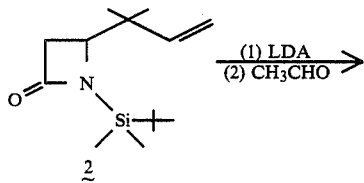

t-Butyldimethylchlorosilane (7.51 g) is added in one portion to an ice-cold, stirred solution of 4-(1,1-dimethyl-yl-prop-2-enyl)-azetidin-2-one (6.54 g) and triethylamine (5.04 g) in anhydrous dimethylformamide (100 ml). The reaction mixture is stirred at 0°–5° C. for 1 hour and then allowed to warm to room temperature. Most of the solvent is removed under vacuum to give a residue which is partitioned between diethyl ether (250 ml) and water. The ethereal phase is washed with 2.5N hydrochloric acid (50 ml), water (3×50 ml), and brine, dried with magnesium sulfate, filtered and evaporated under vacuum to provide crude product which is purified by chromatography on silica gel (20% ether in petroleum ether) to yield 2.

EXAMPLE 2

1-(t-Butyldimethylsilyl)-3-(1-hydroxyethyl)-4-(1,1-dimethylprop-2-enyl)-azetidin-2-one

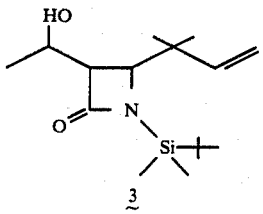

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min. prior to the addition of a solution of 2 (25.0 mmol) in anhydrous tetrahydrofuran (25 ml). After stirring for 15 min. at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5N hydrochloric acid solution (2×50 ml), water (100 ml) and brine and dried over magnesium sulfate. Solvents are removed in vacuo and the residue is chromatographed on silica gel (1:1, ether:petroleum ether) to give the expected product 3.

EXAMPLE 3

1-(t-Butyldimethylsilyl)-3-(1-oxoethyl)-4-(1,1-dimethylprop-2-enyl)-azetidin-2-one

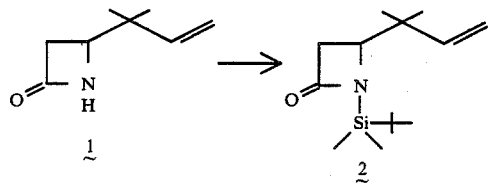

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. A solution of 3 (5.0 mmol) in methylene chloride (15 ml) is added by syringe and the cooling bath is removed. After an additional 1 hr., the reaction mixture is diluted with methylene chloride (100 ml), washed with water (50 ml) and brine and dried over magnesium sulfate. Removal of solvents in vacuo yields crude products which is chromatographed on silica gel (2:1, petroleum ether, ether) to yield 4.

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-4-(1,1-dimethyl-prop-2-enyl)-azetidin-2-one 3 (2.0 mmol) in anhydrous tetrahydro uran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at −78° C. for 15 min., then quenched by addition of saturated aqueous ammonium chloride solution (10 ml). The reaction mixutre is diluted with ether (100 ml) and washed with 2.5N hydrochloric acid solution (25 ml) water (25 ml) and brine. The organic phase is dried over magnesium sulfate and concentrated in vacuo to yield crude products. This material is chromatographed on silica gel (2:1 petroleum ether:ether) to yield 4.

EXAMPLE 4

1-(t-Butyldimethylsilyl)-3-(1-hydroxyethyl)-4-(1,1-dimethylprop-2-enyl)-azetidin-2-one

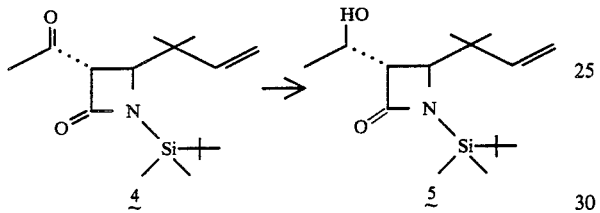

K-Selectride (potassium tri-(sec)-butylborohydride) in tetrahydrofuran (4.8 mmol) is added by syringe to a mixture of potassium iodide (2.0 mol) and 4 (2.0 mmol) in anhydrous ether (20 ml) at room temperature. The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives crude products which is chromatographed on silica gel (1:1 ether:petroleum ether) to yield 1.90 g (95%) of 5.

EXAMPLE 5

1-(t-Butyldimethylsilyl)-3-(1-hydroxyethyl)-4-(1,1-dimethylcarboxymethyl)-azetidin-2-one.

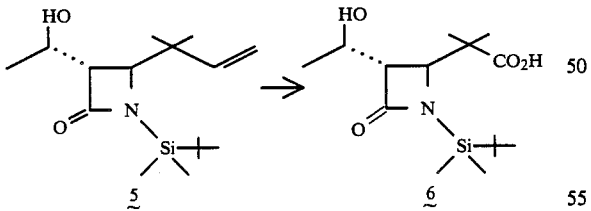

A solution of 1-(t-butyldimethylsilyl)-3-(1-hydroxyethyl)-4-(1,1-dimethyl-prop-2-enyl)-azetidin-2-one (3.0 mmol) in dry methylene chloride (30 ml) is cooled to −78° C. (dry ice-acetone) and a stream of ozone is bubbled through until the reaction mixture becomes blue. The ozone flow is then stopped and the reaction is purged by bubbling through nitrogen until the blue color disappears. Solid m-chloroperbenzoic acid (3.0 mmol) is added and the cold bath is removed. When the reaction mixture reaches room temperature, the flask is fitted with a reflux condenser and the mixture is heated at reflux for three days. Removal of solvents in vacuo gives a crude product which is chromatographed on silica gel (2% glacial acetic acid in methylene chloride) to yield 6.

EXAMPLE 6

1-(t-Butyldimethylsilyl)-3-[1-hydroxyethyl]-4-(1,1-dimethyl-3-p-nitrobenzyloxycarbonyl-2-oxopropyl-)azetidin-2-one

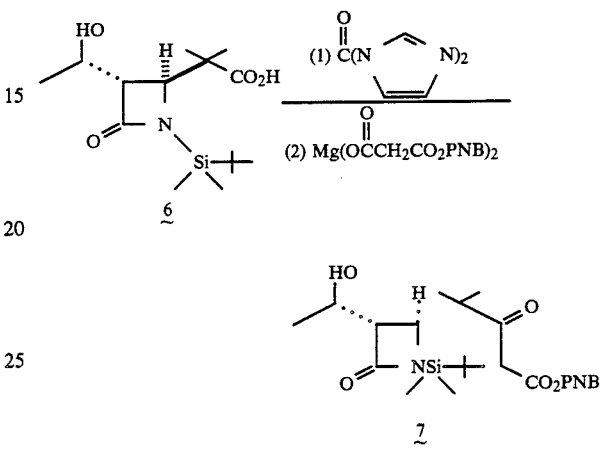

1,1′-Carbonyldiimidazole (1.0 mmol) is added in one portion to a solution of 6 (1.0 mmol) in anhydrous tetrahydrofuran (5 ml) at room temperature. The resulting solution is stirred at room temperature for 6 hours. In a second flask, magnesium ethoxide (5 mmol) is added in one portion to a solution of the mono-p-nitrobenzyl ester of malonic acid (10 mmol) in anhydrous tetrahydrofuran (25 ml). The resulting mixture is stirred at room temperature for 1 hr, then the tetrahydrofuran is removed at the pump and the residue is triturated with ether to yield the magnesium salt. This magnesium salt is then added to the first reaction flask and the resulting mixture is stirred at room temperature for 18 hrs. The reaction mixture is then poured into 50 ml of ether, washed with 0.5N hydrochloric acid solution (20 ml), water (20 ml), saturated aqueous sodium bicarbonate solution (20 ml), brine and dried over magnesium sulfate. Removal of solvents in vacuo gives crude products which is chromatographed on silical gel (ether) to yield 7.

EXAMPLE 7

3-[1-hydroxyethyl]-4-(1,1-dimethyl-p-nitrobenzyloxycarbonyl-2-oxopropyl)-azetidin-2-one

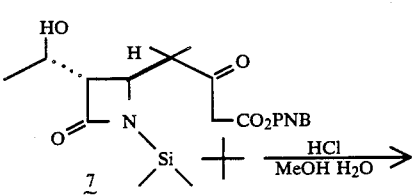

-continued

[Structure 8: HO-substituted azetidinone with CO₂pNB]

8

A solution of 7 (1.0 mmol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs, at room temperature the reaction mixture is diluted with ethyl acetate (25 ml), washed with water (10 ml) and brine, dried over magnesium sulfate and concentrated in vacuo to yield 8.

EXAMPLE 8

Preparation of 3-[1-hydroxyethyl-4-[1,1-dimethyl-3-(4-nitrobenzyl)oxycarbonyl-2-oxo-3-diazopropyl]azetidin-2-one

[Structure 8 → Structure 9]

Triethylamine (263 mg) is added by syringe to a mixture of 8 (253 mg) and p-carboxybenzensulfonylazide (196 mg) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 9.

EXAMPLE 9

Preparation of p-Nitrobenzyl 4,4-dimethyl-6-[1-hydroxyethyl]-1-azabicyclo[3.2.0-]heptan-3,7-dione-2-carboxylate

[Structure 9 → Structure 10]

-continued

[Structure 10: bicyclic product]

10

A suspension of 9 (56.4 mg) and rhodium (II) acetate (0.1 mg) in dry benzene (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield 10.

EXAMPLE 10

Preparation of p-Nitrobenzyloxycarbonylaminoethanethiol $$HS\sim NH_2 \cdot HCl + Cl-COCH_2-\bigcirc-NO_2 \rightarrow$$

$$HS\sim NHCO_2PNB$$

To 600 ml diethyl ether (Et₂O)-75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl₃):8.18 (d, J=8 Hz, aromatic protons ortho to nitro), 7.47 (d, J=8 Hz, aromatic protons meta to nitro), 5.27 (—NH—), 5.20 (s, —CH₂—NH—), 2.67 (m, —CH₂—SH), 1.35 (t, J=8.5 Hz, —SH) in ppm downfield from TMS. IR (CHCl₃) solution): carbonyl-1725 cm⁻¹. M.S.: molecular ion-256, (M-47) at 209, (M-136) at 120, +CH₂φpNO₂ at 136.

EXAMPLE 11

Preparation of p-Nitrobenzyl 4,4-dimethyl-3-[2-(p-nitrobenzyloxycarbonyl)amino ethylthio]-6-1-hydroxyethyl)-1-azabicyclo[3.2.0]-hept-2-en-7-one-2-carboxylate

[Structure 10]

15
-continued

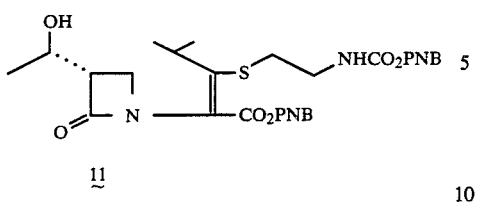

11 p-Nitrobenzyl 4,4-dimethyl 6-[1-hydroxyethyl)-1-azabicyclo[3.2.0]heptan-3,7-dione-2-carboxylate (51 mg) is dissolved in acetonitrile (3 ml) and the resulting solution is cooled to 0° C. Diisopropylethylamine (22 mg) is added by syringe and the resulting solution is stirred at 0° C. for 1 minute prior to the addition of a solution of freshly recrystallized p-toluene sulfonic anhydride (51 mg) in dry acetonitrile (1 ml). The resulting solution is stirred at 0° C. for 1 hour to provide p-nitrobenzyl 4,4-dimethyl 3-(p-toluenesulfonyloxy)-6-[1-hydroxyethyl]-1-azabicyclo[3.2.0]hept-2-en-7-one-2-carboxylate, then cooled to −25° C. Diisopropylethylamine (80.5 mg) is added by syringe followed shortly thereafter by a solution of N-p-nitrobenzyloxycarbonyl-cysteamine (40 mg) in 1 ml of dry acetonitrile. The reaction mixture is then stored in a refrigerator for 70 hr. The mixture is diluted with 25 ml of ethyl acetate washed with brine and dried over magnesium sulfate. Solvents are removed in vacuo to yield a yellow oil which is chromatographed on a silica gel plate to yield p-nitrobenzyl 4,4-dimethyl-3-[2-(p-nitrobenzyloxycarbonyl)aminoethylthio]-6-[1-hydroxyethyl]-1-azabicyclo[3.2.0]hept-2-en-7-dione-2-carboxylate.

EXAMPLE 12

Preparation of 4,4-dimethyl thienamycin

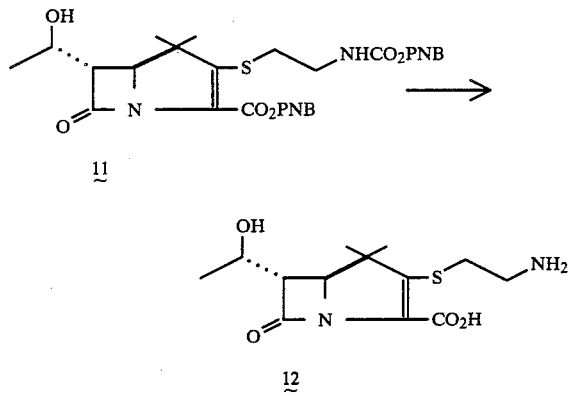

A mixture of N-p-nitrobenzyloxycarbonyl 4,4-dimethyl thienamycin p-nitrobenzyl ester 11(10 mg) and 10% Pd/C-Bolhofer type in tetrahydrofuran (2 ml), 0.1M dipotassium hydrogen phosphate solution (1.4 ml) and 2-propanol (0.2 ml) is hydrogenated at 40 psi on the Parr shaker for 30 minutes. The mixture is then filtered and the catalyst is washed with water. The combined filtrate and washings are extracted with ethyl acetate-ethyl ether then concentrated to ~3 ml and lyophilized to give 4,4-dimethylthienamycin 12.

16
EXAMPLE 13

Preparation of 3,3-Dimethyl-1,4-pentadiene

1

Procedure a

β,β-Dimethylglutaric acid (obtained from Aldrich Chemical Company) (one mole), is refluxed for 2 hours with thionyl chloride (68% excess). After removal of excess thionyl chloride, absolute ethanol (109% excess) is added slowly. The mixture is refluxed for 3 hours then distilled to collect the product, diethyl β,β-dimethylglutarate (98% yield).

To a suspension of lithium aluminum hydride (24 g) in ether (860 ml) is added dropwise with rapid stirring a solution of diethyl β,β-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p.95° at 1.0 mm. The 3,3-dimethyl-1,5-pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1,5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

Procedure b

At −40° C., 1,3-dichloro-3-methylbutane (50 g) is mixed with aluminum chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylguinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 14

Preparation of 3-methyl-1,4-pentadiene

2

Following the procedure of Example 1(a), but replacing β,β-dimethylglutaric acid with an equivalent amount of β-methylglutaric acid, 3-methyl-1,4-pentadiene is obtained.

EXAMPLE 15

Preparation of 4-(1,1-dimethyl-pro-2-enyl)azetidin-2-one

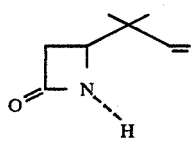

3

In a sealed tube, 3,3-dimethyl-1,4-pentadiene (9.6 g) and chlorosulfonyl isocyanate (14.2 g) are allowed to stand at room temperature for 6 days. The resulting mixture is diluted with methylene chloride and added slowly to a stirred aqueous solution which contains 20 g of $Na_2SO_3$ and 50 g of $K_2HPO_4$ at 0°–5° C. for 30 min. The organic layer is separated and dried over $Mg_2SO_4$. After evaporation, the crude product is chromatographed on silica gel GF eluting with EtOAc to give 3.

EXAMPLE 15a

Preparation of 4-(1-methyl-pro-2-enyl)azetidin-2-one

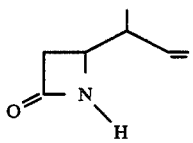

4

Following the procedure of Example 3, but replacing 3,3-dimethyl-1,4-pentadiene with 3-methyl-1,4-pentadiene, the title compound 4 is obtained.

EXAMPLE 16

Following the procedure of the foregoing Examples, the following azetidinones are obtained when the indicated change in reagents is made.

| | $R^1$ | $R^2$ |
|---|---|---|
| 1. | $CH_3$ | H |
| 2. | $CH_3$ | Et |
| 3. | Et | Et |
| 4. | $CH_3CH_2CH_2$ | $CH_3$ |
| 5. | $CH_3$\\$CH$/$CH_3$ | $CH_3$ |
| 6. | cyclopropyl | H |
| 7. | Ph— (ph = phenyl) | $CH_3$ |
| 8. | $PhCH_2$— | $CH_3$ |
| 9. | $R^1$ and $R^2$ are joined together to form a spirocyclopropyl | |

EXAMPLE 17

Following the procedure of Examples 2 and 3, but using the azetidinones obtained from Example 16, the following azetidinones are obtained.

| Compound | $R^1$ | $R^2$ |
|---|---|---|
| (1.) | $CH_3$ | H |
| (2.) | $CH_3$ | Et |
| (3.) | Et | Et |
| (4.) | $CH_3CH_2CH_2$ | $CH_3$ |
| (5.) | $CH_3$\\$CH$/$CH_3$ | $CH_3$ |
| (6.) | cyclopropyl | H |
| (7.) | Ph— | $CH_3$ |
| (8.) | $PhCH_2$— | $CH_3$ |
| (9.) | $R^1$ and $R^2$ joined together to form a spiro-cyclopropyl. | |

EXAMPLE 18

Following the procedure of the foregoing Examples, the following species of the present invention are obtained when the azetidinones of Example 17 are substituted in equivalent amounts, respectively, for the azetidinone of Examples 1–12.

| Compound | $R^1$ | $R^2$ | Remarks |
|---|---|---|---|
| (1.) | $CH_3CH_2$— | $CH_3$ | |
| (2.) | $CH_3CH_2CH_2$— | $CH_3CH_2$— | |
| (3.) | $CH_3$\\$CH$—/$CH_3$ | $CH_3$ | |
| (4.) | cyclopropyl | $CH_3$ | |
| (5.) | phenyl | $CH_3$ | |
| (6.) | benzyl ($PhCH_2$—) | $CH_3$ | |
| (7.) | $R_1 + R_2$ = spiro-cyclopropyl | | |

EXAMPLE 19

Preparation of Pharmaceutical Compositions

One such unit dosage form is prepared by mixing 120 mg of 1,1-dimethyl-6-(1-hydroxyethyl)-2-(2-aminoethylthio)-1-carbadethiapen-2-em-3-carboxylic acid with 20 mg of lactose and 5 mg of magnesium stearate. The 145 mg. mixture is placed into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules or compressed tablets can also be prepared. The following examples are illustrative of the preparation of pharmaceutical formulations:

| TABLET | PER TABLET |
|---|---|
| 1,1-dimethyl-6-(1-hydroxyethyl)-2-(2-aminoethylthio)-1-carbadethiapen-2-em-3-carboxylic acid | 125 mg. |
| Dicalcium Phosphate | 192 mg. |
| Cornstarch, U.S.P. | 6 mg. |
| Lactose, U.S.P. | 190 mg. |
| Magnesium Stearate | Balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1,1-dimethyl-6-(1-hydroxyethyl)-2-(2-aminoethylthio-1-carbadethia-)pen-2-em-3-carboxylic acid | 500 mg. |
| Diluent: Sterile Water for Injection | 5 cc. |
| OPTHALMIC SOLUTION | |
| 1,1-dimethyl-6-(1-hydroxyethyl)-2-(2-aminoethylthio-1-carbadethia)-pen-2-em-3-carboxylic acid | 100 mg. |
| Hydroxypropylmethyl cellulose | 5 mg. |
| Sterile water to | 1 ml. |
| OTIC SOLUTION | |
| 1,1-dimethyl-6-(1-hydroxyethyl)-2-(2-aminoethylthio-1-carbadethia)-pen-2-em-3-carboxylic acid | 100 mg. |
| Benzalkonium chloride | 0.1 mg. |
| Sterile water to | 1 ml. |
| TOPICAL OINTMENT | |
| 1,1-dimethyl-6-(1-hydroxyethyl)-2-(2-aminoethylthio-1-carbadethia-pen-2-em-3-carboxylic acid | 100 mg. |
| Polyethylene Glycol 4000 U.S.P. | 400 mg. |
| Polyethylene Glycol 400 U.S.P. | 1.0 gram. |

What is claimed is:

1. A compound having the formula:

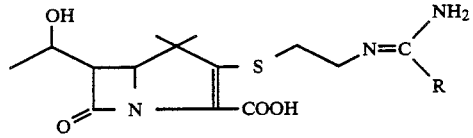

wherein R is H, $NH_2$ or $CH_3$.

2. A compound of claim 1 wherein R is $CH_3$.
3. A compound of claim 1 wherein R is $NH_2$.
4. A compound of claim 1 wherein R is H.

* * * * *